United States Patent
Zack et al.

(10) Patent No.: US 9,655,882 B2
(45) Date of Patent: *May 23, 2017

(54) COMPOSITIONS AND METHODS FOR TREATMENT OF NEURODEGENERATIVE DISEASE

(71) Applicant: THE JOHNS HOPKINS UNIVERSITY, Baltimore, MD (US)

(72) Inventors: Donald J. Zack, Baltimore, MD (US); Zhiyong Yang, Baltimore, MD (US); Cynthia Berlinicke, Baltimore, MD (US); Harry Quigley, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 98 days.

This patent is subject to a terminal disclaimer.

(21) Appl. No.: 14/626,524

(22) Filed: Feb. 19, 2015

(65) Prior Publication Data

US 2015/0258061 A1  Sep. 17, 2015

Related U.S. Application Data (62) Division of application No. 13/058,171, filed as application No. PCT/US2009/053241 on Aug. 8, 2009, now Pat. No. 8,993,615.

(60) Provisional application No. 61/142,377, filed on Jan. 4, 2009, provisional application No. 61/188,362, filed on Aug. 8, 2008.

(51) Int. Cl.
| | |
|---|---|
| *A61K 31/404* | (2006.01) |
| *A61K 31/00* | (2006.01) |
| *A61K 45/06* | (2006.01) |
| *A61K 31/496* | (2006.01) |

(52) U.S. Cl.
CPC ............ *A61K 31/404* (2013.01); *A61K 31/00* (2013.01); *A61K 31/496* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,573,293 B2 | 6/2003 | Tang et al. | |
| 7,125,905 B2 | 10/2006 | Tang et al. | |
| 7,211,600 B2 | 5/2007 | Lipson et al. | |
| 8,993,615 B2* | 3/2015 | Zack ................. | A61K 31/00 514/414 |
| 2002/0156292 A1* | 10/2002 | Tang ................. | C07D 207/33 548/487 |
| 2003/0105151 A1* | 6/2003 | Tang ................. | C07D 209/34 514/414 |
| 2007/0185069 A1 | 8/2007 | Plum et al. | |

FOREIGN PATENT DOCUMENTS

WO  2005/047273 A1  5/2005

OTHER PUBLICATIONS

Plowman et al., Receptor tyrosine kinases as targets for drug intervention, Drug News and Perspectives 7(6): 334-339, Aug. 1994.*

Takahashi et el., "A Novel Vascular Endothelial Growth Factor Receptor 2 Inhibitor, SU11248, Suppresses Choroidal Neovascularization In Vivo", Journal of Ocular Pharmacology and Therapeutics, vol. 22, No. 4, 2006.

International Preliminary Report on Patentability, mailed Apr. 1, 2010 for PCT/US2009/053241.

Plowman et al., "Receptor tyrosine kinases as targets for drug intervention," Drug News and Perspectives 7(6): 334-339, Aug. 1994.

International Search Report, mailed Aug. 8, 2008 for PCT/US2009/053241.

* cited by examiner

*Primary Examiner* — Svetlana M Ivanova
(74) *Attorney, Agent, or Firm* — Michael Best & Friedrich LLP; Jeffrey W. Childers (57) ABSTRACT

Compounds, compositions, kits and methods for treating conditions related to neurodegeneration or ocular disease, are disclosed.

8 Claims, 5 Drawing Sheets

COMPOSITIONS AND METHODS FOR TREATMENT OF NEURODEGENERATIVE DISEASE

CROSS REFERENCE TO RELATED APPLICATION

This application is a divisional of U.S. patent application Ser. No. 13/058,171, filed Apr. 4, 2011, which is a 35 U.S.C. 371 National Stage Entry of International Application No. PCT/US2009/053241 having an international filing date of Aug. 8, 2009, which claims the benefit of priority to U.S. Provisional Application Nos. 61/142,377, filed Jan. 4, 2009, and 61/188,362, filed Aug. 8, 2008, the entire disclosures of which are hereby incorporated herein in their entirety.

STATEMENT OF RIGHTS TO INVENTIONS MADE UNDER FEDERALLY SPONSORED RESEARCH

This work was supported in part by the NIH grant no. NIH R21EY017155. The government has certain rights in the invention.

BACKGROUND OF THE INVENTION

Neurodegenerative disorders afflict numerous patients throughout the world, and treatments are often unsatisfactory. For example, glaucoma (a disease or condition that results in damage to the optic nerve) is a major cause of vision loss and blindness, especially in the elderly. Although various treatments for glaucoma exist, many such treatments are of limited efficacy and/or have significant side effects. For example, while reduction of intraocular pressure, generally through pharmacologic or surgical intervention, is presently the mainstay of glaucoma therapy, such therapies are often only partially effective and generally cannot restore neuronal cell function once such function has been lost. Thus, new methods for treatment of ocular and/or neurodegenerative disorders or diseases, including glaucoma, are needed.

SUMMARY OF THE INVENTION

The invention relates generally to the discovery that certain compounds (including sunitinib (marketed under the trade name SUTENT) and other protein kinase inhibitors (e.g., Flt3 inhibitors)) can promote the survival and/or neurite outgrowth of retinal ganglion cells (RGCs).

In one aspect, the invention relates to a method of treating or preventing a neurodegenerative disease or disorder, the method comprising administering to a subject in need thereof an effective amount of a receptor tyrosine kinase inhibitor, or a pharmaceutically acceptable salt thereof, to the subject, thereby treating or preventing the neurodegenerative disease or disorder.

In one aspect, the invention relates to a method of treating or preventing a neurodegenerative disease or disorder, the method comprising administering to a subject in need thereof an effective amount of an flt3 inhibitor, or a pharmaceutically acceptable salt thereof, to the subject, thereby treating or preventing the neurodegenerative disease or disorder.

In another aspect, the invention relates to a method of treating or preventing a neurodegenerative disease or disorder, the method comprising administering to a subject in need thereof an effective amount of a src inhibitor, or a pharmaceutically acceptable salt thereof, to the subject, thereby treating or preventing the neurodegenerative disease or disorder.

In certain embodiments, the neurodegenerative disease or disorder is a neurodegenerative disease or disorder that is not associated with excessive angiogenesis. In certain embodiments, the neurodegenerative disease or disorder is glaucoma. In certain embodiments, the neurodegenerative disease or disorder is glaucoma that is not neovascular glaucoma. In certain embodiments, the flt3 inhibitor is sunitinib.

In certain embodiments, the step of administering the compound includes administering the compound in a pharmaceutically acceptable composition. In certain embodiments, the pharmaceutically acceptable composition is essentially free of an additional angiogenesis inhibitor (e.g., other than the flt3 inhibitor, no angiogenesis inhibitor is present).

In another aspect, the invention relates to a method of treating or preventing a neurodegenerative disease or disorder, the method comprising administering to a subject in need thereof an effective amount of a pharmaceutical composition consisting essentially of sunitinib, or a pharmaceutically acceptable salt thereof, thereby treating or preventing the neurodegenerative disease or disorder.

In certain embodiments, the neurodegenerative disease or disorder is glaucoma. In certain embodiments, the glaucoma is not neovascular glaucoma.

In certain embodiments, the subject is a mammal. In certain embodiments, the subject is a human.

In certain embodiments, the method further includes the step of monitoring the subject to determine the efficacy of treatment.

In another aspect, the invention provides a method for treating or preventing neuronal cell loss in a subject in need of such treatment, the method comprising administering to the subject an effective amount of sunitinib, or a pharmaceutically acceptable salt thereof, thereby treating or preventing neuronal cell loss in the subject.

In certain embodiments of the methods of the invention, the effective amount of the receptor tyrosine kinase inhibitor, flt3 inhibitor, src inhibitor or sunitinib, or a pharmaceutically acceptable salt thereof, is in a range of 0.0001 to about 100 mg per kilogram of body weight per day.

In certain embodiments, the compound (e.g., the receptor tyrosine kinase inhibitor, flt3 inhibitor, src inhibitor, c-kit inhibitor, met inhibitor, or sunitinib, or a pharmaceutically acceptable salt thereof), is administered to the subject by the method selected from the group consisting of: oral, topical (including ocular), parenteral, intravitreal, and systemic.

In certain embodiments of the methods of the invention, an additional therapeutic agent is administered to the subject. In certain embodiments, the additional therapeutic agent is selected from the group consisting of beta-blockers, alpha-agonists, carbonic anhydrase inhibitors, prostaglandins or prostaglandin analogs, miotic or cholinergic agents, epinephrine compounds, forskolin, or neuroprotective compounds.

In another aspect, the invention relates to a method for treating or preventing neuronal cell death, the method comprising contacting a neuronal cell with an effective amount of sunitinib, or a pharmaceutically acceptable salt thereof, thereby treating or preventing neuronal cell death.

In another aspect, the invention relates to a kit comprising sunitinib, or a pharmaceutically acceptable salt thereof, in unit dosage form, together with instructions for using sunitinib, or a pharmaceutically acceptable salt thereof, for treating or preventing a neurodegenerative disease or disorder.

In another aspect, the invention relates to a method of treating or preventing a neurodegenerative disease or disorder, the method comprising administering to a subject in need thereof an effective amount of a compound capable of inhibiting Flt3, thereby treating or preventing the neurodegenerative disease or disorder.

In another aspect, the invention relates to a method of treating or preventing NMDA-induced excitotoxicity, the method comprising administering to a subject in need thereof an effective amount of a compound capable of inhibiting Flt3, thereby treating or preventing the neurodegenerative disease or disorder.

In another aspect, the invention relates to a method of stimulating growth or regeneration of neurites, the method comprising administering to a subject in need thereof an effective amount of a compound capable of inhibiting Flt3, thereby stimulating growth or regeneration of neurites.

In another aspect, the invention relates to a method of preventing apoptosis of neuronal cells, the method comprising administering to a subject in need thereof an effective amount of a compound capable of inhibiting a receptor tyrosine kinase or Flt3, thereby stimulating regeneration of neuronal axons.

In another aspect, the invention relates to a method of preventing cell death in a neuronal cell, the method comprising administering to a cell in need thereof an effective amount of a compound capable of inhibiting a receptor tyrosine kinase or Flt3, thereby preventing cell death in the neuronal cell.

In another aspect, the invention relates to a method of treating traumatic injury to a neuronal cell, the method comprising administering to a neuronal cell in need thereof an effective amount of a compound capable of inhibiting a receptor tyrosine kinase or Flt3, thereby treating traumatic injury in the neuronal cell. In certain embodiments, the traumatic injury is an ischemic condition of the nervous system. In certain embodiments, the ischemic condition of the nervous system is stroke.

In certain embodiments, the compound capable of inhibiting a receptor tyrosine kinase or Flt3 is sunitinib or lestaurtanib.

In another aspect, the invention relates to a method of treating or preventing a neurodegenerative disease or disorder, the method comprising administering to a subject in need thereof an effective amount of a compounds selected from the group consisting of an flt3 inhibitor, a phosphatase (PP2A or PP1) inhibitor, a p38 MAP kinase inhibitor, a TGF-beta receptor inhibitor, and a RNA-dependent protein kinase inhibitor, or a pharmaceutically acceptable salt thereof, to the subject, thereby treating or preventing the neurodegenerative disease or disorder.

In another aspect, the invention relates to a method of treating or preventing a neurodegenerative disease or disorder, the method comprising administering to a subject in need thereof an effective amount of a compound selected from the group consisting of a c-kit, a met inhibitor, or a src inhibitor, or a pharmaceutically acceptable salt thereof, to the subject, thereby treating or preventing the neurodegenerative disease or disorder.

In another aspect, the invention relates to a method of treating or preventing a neurodegenerative disease or disorder, the method comprising increasing the activity in a subject of an enzyme selected from the group consisting of a cyclin dependent kinase (CDK), c-Jun N-terminal kinases 2 (JNK2), kinase insert domain receptor (KDR), spleen tyrosine kinase (SYK), and glycogen synthase kinase 3 (GSK3), thereby treating or preventing the neurodegenerative disease or disorder.

In another aspect, the invention relates to a method of treating or preventing a neurodegenerative disease or disorder, the method comprising administering to a subject in need thereof an effective amount of a sunitinib, or a pharmaceutically acceptable salt thereof, thereby treating or preventing the neurodegenerative disease or disorder.

In another aspect, the invention relates to a method of treating or preventing a neurodegenerative disease or disorder, the method comprising administering to a subject in need thereof an effective amount of a compound represented by the following structure (I):

wherein:

$R_1$ is selected from the group consisting of hydrogen, halo, alkyl, cyclkoalkyl, aryl, heteroaryl, heteroalicyclic, hydroxy, alkoxy, —(CO)$R_{15}$, —$NR_{13}R_{14}$, —(CH$_2$)$_r R_{16}$ and —C(O)$NR_8R_9$;

$R_2$ is selected from the group consisting of hydrogen, halo, alkyl, trihalomethyl, hydroxy, alkoxy, cyano, —$NR_{13}R_{14}$, —$NR_{13}C(O)R_{14}$, —C(O)$R_{15}$, aryl, heteroaryl, —S(O)$_2$$NR_{13}R_{14}$ and —SO$_2$$R_{20}$ (wherein $R_{20}$ is alkyl, aryl, aralkyl, heteroaryl and heteroaralkyl);

$R_3$ is selected from the group consisting of hydrogen, halogen, alkyl, trihalomethyl, hydroxy, alkoxy, —(CO)$R_{15}$, —$NR_{13}R_{14}$, aryl, heteroaryl, —$NR_{13}S(O)_2R_{14}$, —S(O)$_2R_{13}R_{14}$, —$NR_{13}C(O)R_{14}$, —$NR_{13}C(O)OR_{14}$ and —SO$_2R_{20}$ (wherein $R_{20}$ is alkyl, aryl, aralkyl, heteroaryl and heteroaralkyl);

$R_4$ is selected from the group consisting of hydrogen, halogen, alkyl, hydroxy, alkoxy and —$NR_{13}R_{14}$;

$R_5$ is selected from the group consisting of hydrogen, alkyl and —C(O)$R_{10}$;

$R_6$ is selected from the group consisting of hydrogen, alkyl and —C(O)$R_{10}$;

$R_7$ is selected from the group consisting of hydrogen, alkyl, aryl, heteroaryl, —C(O)$R_{17}$ and —C(O)$R_{10}$; or $R_6$ and $R_7$ may combine to form a group selected from the group consisting of —(CH$_2$)$_4$—, —(CH$_2$)$_5$— and —(CH$_2$)$_6$—; with the proviso that at least one of $R_5$, $R_6$ or $R_7$ must be —C(O)$R_{10}$;

$R_8$ and $R_9$ are independently selected from the group consisting of hydrogen, alkyl and aryl;

$R_{10}$ is selected from the group consisting of hydroxy, alkoxy, aryloxy, —N($R_{11}$) (CH$_2$)$_n R_{12}$, and —$NR_{13}R_{14}$;

$R_{11}$ is selected from the group consisting of hydrogen and alkyl;

$R_{12}$ is selected from the group consisting of —$NR_{13}R_{14}$, hydroxy, —C(O)$R_{15}$, aryl, heteroaryl, —N$^+$(O$^-$)$R_{13}R_{14}$, —N(OH)$R_{13}$, and —NHC(O)$R_a$ (wherein $R_a$ is unsubstituted alkyl, haloalkyl, or aralkyl);

$R_{13}$ and $R_{14}$ are independently selected from the group consisting of hydrogen, alkyl, cyanoalkyl, cycloalkyl, aryl and heteroaryl; or $R_{13}$ and $R_{14}$ may combine to form a heterocyclo group;

$R_{15}$ is selected from the group consisting of hydrogen, hydroxy, alkoxy and aryloxy;

$R_{16}$ is selected from the group consisting of hydroxy, —C(O)$R_{15}$, —N$R_{13}R_{14}$ and —C(O)N$R_{13}R_{14}$;

$R_{17}$ is selected from the group consisting of alkyl, cycloalkyl, aryl and heteroaryl;

$R_{20}$ is alkyl, aryl, aralkyl or heteroaryl; and n and r are independently 1, 2, 3, or 4;

or a pharmaceutically acceptable salt thereof;

thereby treating or preventing the neurodegenerative disease or disorder.

In certain embodiments, a compound used in the methods, kits, or uses described herein is selected from sunitinib, SU11274, SU5416, and SU6656; more preferably, the compound is sunitinib or SU6656.

The invention also relates to the use of any of the compounds of the invention for the treatment and/or prevention of a neurodegenerative disease or disorder (including traumatic injury to a neuronal cell), prevention of cell death or apoptosis of a neuronal cell (including in vitro or in a subject), stimulating growth or regeneration of neurites from a neuronal cell, and/or treating or preventing NMDA-induced excitotoxicity.

The invention also relates to the use of any of the compounds herein for the preparation of a medicament for the treatment and/or prevention of a neurodegenerative disease or disorder (including traumatic injury to a neuronal cell), prevention of cell death or apoptosis of a neuronal cell (including in a subject), stimulating growth or regeneration of neurites form a neuronal cell, and/or treating or preventing NMDA-induced excitotoxicity.

Other features and advantages of the invention will be apparent from the detailed description, and from the claims.

BRIEF DESCRIPTION OF THE DRAWINGS

FIGS. 1a and 1B show the screening of kinase inhibitors for RGC survival and neurite growth promoting activities. Purified mouse RGCs were grown in Neurobasal, 2% B27, 1% N2 supplement, 0.5 mM glutamine. 2 µM forskolin was present in all the conditions except vehicle control with DMSO (dark bar), for 60 hours. Increasing concentrations of kinase inhibitors were present in the media as indicated. Viability and neurite growth of RGCs were assayed by a combined staining with Calcein AM, Hoechst, and Ethidium Homodimer-1. The images were taken and processed by Cellomics Kineticscan. RTK, receptor tyrosine kinase; KDR: kinase insert domain receptor; SYK: spleen tyrosine kinase; CDK: cyclin-dependent kinase; GSK3: glycogen synthase kinase3; JNK: Jun-N-terminal kinase. Error bars: S.E.M.

In FIG. 2A and FIG. 2B, RGC somas and neurites were revealed by Calcein AM staining, after 60 hours culture in the presence of DMSO (1:1000) (FIG. 2A), or forskolin (2.5 µM) (FIG. 2B). Scale bar: 10 µm. RGC survival and neurite growth were quantitatively measured as average surviving RGCs/field (4 mm$^2$) (FIG. 2C), total neurite length per RGC (FIG. 2D), average neurite length per RGC (FIG. 2E), and total neurite count per RGC (FIG. 2F). Error bars: S.E.M.

DETAILED DESCRIPTION OF THE INVENTION

The invention relates generally to the discovery that certain compounds, including sunitinib (marketed under the trade name SUTENT) which can inhibit protein kinases such as flt3, can promote the survival and/or neurite outgrowth of retinal ganglion cells (RGCs). In certain embodiments, a compound is used according to this invention to prevent the death of damaged neuronal cells. In other embodiments, a compound is used according to this invention to promote the growth or regeneration of all or part of a neuronal cell (e.g., growth of neurites such as axons, dendrites, and the like). The invention also relates to methods for treating neurodegenerative diseases and disorders by administration of such compounds.

The invention further relates to compounds and methods for treating or preventing neurodegenerative diseases and disorders by increasing the activity of an enzyme selected from the group consisting of a cyclin dependent kinase (CDK), c-Jun N-terminal kinases 2 (JNK2), kinase insert domain receptor (KDR), spleen tyrosine kinase (SYK), and glycogen synthase kinase 3 (GSK3), thereby treating or preventing the neurodegenerative disease or disorder.

DEFINITIONS

By the term "decrease" is meant inhibit, suppress, attenuate, diminish, arrest, or stabilize a symptom of a neurodegenerative disease or disorder.

By "neurodegenerative disease or disorder" is meant a disorder (including a neuropathy) associated with degeneration or dysfunction of neurons or other neural cells such as retinal ganglion cells. A neurodegenerative disease or disorder can be any disease or condition in which decreased function or dysfunction of neurons, or loss or neurons or other neural cells, can occur. Such conditions include, without limitation, glaucoma, and neurodegenerative disorders such as or associated with alcoholism, Alexander's disease, Alper's disease, Alzheimer's disease, amyotrophic lateral sclerosis (Lou Gehrig's Disease), ataxia telangiectasia, Batten disease (also known as Spielmeyer-Vogt-Sjogren-Batten disease), bovine spongiform encephalopathy (BSE), Canavan disease, Cockayne syndrome, corticobasal degeneration, Creutzfeldt-Jakob disease, diabetic neuropathy, frontotemporal lobar degeneration, Huntington's disease, HIV-associated dementia, Kennedy's disease, Krabbe's disease, Lewy body dementia, neuroborreliosis, Machado-Joseph disease (Spinocerebellar ataxia type 3), wet or dry macular degeneration, Multiple System Atrophy, multiple sclerosis, Niemann Pick disease, Parkinson's disease, Pelizaeus-Merzbacher Disease, photoreceptor degenerative diseases such as retinitis pigmentosa and associated diseases, Pick's disease, primary lateral sclerosis, prion diseases, Progressive Supranuclear Palsy, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), spinal muscular atrophy, Steele-Richardson-Olszewski disease, and tabes dorsalis. Traumatic injury or other damage to neuronal cells (e.g., trauma due to accident, blunt-force injury, gunshot injury, spinal cord injury, ischemic conditions of the nervous system such as stroke, cell damage due to aging or oxidative stress, and the like) is also intended to be included within the language "neurodegenerative disease or disorder". In certain embodiments, the neurodegenerative disease or disorder is a disease or disorder that is not associated with excessive angiogenesis, for example, glaucoma that is not neovascular glaucoma.

The term "inhibit" or "inhibits" means to decrease, suppress, attenuate, diminish, arrest, or stabilize the development or progression of a disease or disorder, or the activity of a biological pathway, e.g., by at least 10, 20, 30, 40, 50, 60, 70, 80, 90, 95, 98, or 99% compared to an untreated control subject, cell, or biological pathway.

The term "$IC_{50}$" means the dose of a drug which is half the maximal inhibitory concentration.

The term "neurite" means a projection from the cell body of a neuron including, e.g., an axon or a dendrite.

The term "subject" refers to human or non-human animals, typically mammalian animals, such as primates (humans, apes, gibbons, chimpanzees, orangutans, macaques), domestic animals (dogs and cats), farm animals (horses, cattle, goats, sheep, pigs) and experimental animals (mouse, rat, rabbit, guinea pig). Subjects include animal disease models (e.g., rats or mice used in experiments, e.g., optic crush experiments).

The phrases "parenteral administration" and "administered parenterally" as used herein means modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "therapeutically effective amount" refers to an amount sufficient to produce the desired effect, e.g., to reduce or ameliorate the severity, duration, progression, or onset of a disease, condition, or disorder (e.g., a disease, condition, or disorder related to loss of neuronal cells or cell function), or one or more symptoms thereof; prevent the advancement of a disease, condition, or disorder; cause the regression of a disease, condition, or disorder; prevent the recurrence, development, onset or progression of a symptom associated with a disease, condition, or disorder; or enhance or improve the prophylactic or therapeutic effect(s) of another therapy. An effective amount of a compound according to this invention can range from, e.g., about 0.001 mg/kg to about 1000 mg/kg, or in certain embodiments, about 0.01 mg/kg to about 100 mg/kg, or in certain embodiments, about 0.1 mg/kg to about 50 mg/kg. Effective doses will also vary, as recognized by those skilled in the art, depending on the disorder treated, route of administration, excipient usage, the age and sex of the subject, and the possibility of co-usage with other therapeutic treatments such as use of other agents. It will be appreciated that an amount of a compound required for achieving, e.g., neuroprotective activity, may be different from the amount of compound effective for another purpose (e.g., antineoplastic activity).

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "treatment" is intended to encompass also prophylaxis, therapy and cure.

Compounds

In certain embodiments, the compound is a receptor tyrosine kinase inhibitor. In certain embodiments, the compound is an flt3 inhibitor. The term "flt3 inhibitor", as used herein, refers to a compound having partial or total flt3-inhibitory activity at a therapeutically relevant dose. Such a compound can be a selective inhibitor of flt3 (i.e., a compound that inhibits flt3 but has relatively little inhibition of other receptor tyrosine kinases.

Examples of selective or non-selective flt3 inhibitors include sunitinib, soratinib, lestaurtinib, bis-(5-hydroxy-1H-indol-2-yl)methanone, and (5-phenyl-thiazol-2-yl)-(4-(2-pyrrolidin-1-yl-ethoxy)-phenyl)-amine (see, e.g., PCT Publication No. WO2005/047273, incorporated herein by reference).

In certain embodiments, the compound is represented by the following structure (I):

wherein:

$R_1$ is selected from the group consisting of hydrogen, halo, alkyl, cyclkoalkyl, aryl, heteroaryl, heteroalicyclic, hydroxy, alkoxy, —(CO)$R_{15}$, —$NR_{13}R_{14}$, —$(CH_2)_rR_{16}$ and —C(O)$NR_8R_9$;

$R_2$ is selected from the group consisting of hydrogen, halo, alkyl, trihalomethyl, hydroxy, alkoxy, cyano, —$NR_{13}R_{14}$, —$NR_{13}C(O)R_{14}$, —C(O)$R_{15}$, aryl, heteroaryl, —S(O)$_2$ $NR_{13}R_{14}$ and —SO$_2R_{20}$ (wherein $R_{20}$ is alkyl, aryl, aralkyl, heteroaryl and heteroaralkyl);

$R_3$ is selected from the group consisting of hydrogen, halogen, alkyl, trihalomethyl, hydroxy, alkoxy, —(CO) $R_{15}$, —$NR_{13}R_{14}$, aryl, heteroaryl, —$NR_{13}S(O)_2R_{14}$, —S(O)$_2R_{13}R_{14}$, —$NR_{13}C(O)R_{14}$, —$NR_{13}C(O)OR_{14}$ and —SO$_2R_{20}$ (wherein $R_{20}$ is alkyl, aryl, aralkyl, heteroaryl and heteroaralkyl);

$R_4$ is selected from the group consisting of hydrogen, halogen, alkyl, hydroxy, alkoxy and —$NR_{13}R_{14}$;

$R_5$ is selected from the group consisting of hydrogen, alkyl and —C(O)$R_{10}$;

$R_6$ is selected from the group consisting of hydrogen, alkyl and —C(O)$R_{10}$;

$R_7$ is selected from the group consisting of hydrogen, alkyl, aryl, heteroaryl, —C(O)$R_{17}$ and —C(O)$R_{10}$; or $R_6$ and $R_7$ may combine to form a group selected from the group consisting of —(CH$_2$)$_4$—, —(CH$_2$)$_5$— and —(CH$_2$)$_6$—; with the proviso that at least one of $R_5$, $R_6$ or $R_7$ must be —C(O)$R_{10}$;

$R_8$ and $R_9$ are independently selected from the group consisting of hydrogen, alkyl and aryl;

$R_{10}$ is selected from the group consisting of hydroxy, alkoxy, aryloxy, —N($R_{11}$)(CH$_2$)$_n$$R_{12}$, and —NR$_{13}$R$_{14}$;

$R_{11}$ is selected from the group consisting of hydrogen and alkyl;

$R_{12}$ is selected from the group consisting of —NR$_{13}$R$_{14}$, hydroxy, —C(O)R$_{15}$, aryl, heteroaryl, —N$^+$(O$^-$)R$_{13}$R$_{14}$, —N(OH)R$_{13}$, and —NHC(O)R$_a$ (wherein R$_a$ is unsubstituted alkyl, haloalkyl, or aralkyl);

$R_{13}$ and $R_{14}$ are independently selected from the group consisting of hydrogen, alkyl, cyanoalkyl, cycloalkyl, aryl and heteroaryl; or $R_{13}$ and $R_{14}$ may combine to form a heterocyclo group;

$R_{15}$ is selected from the group consisting of hydrogen, hydroxy, alkoxy and aryloxy;

$R_{16}$ is selected from the group consisting of hydroxy, —C(O)R$_{15}$, —NR$_{13}$R$_{14}$ and —C(O)NR$_{13}$R$_{14}$;

$R_{17}$ is selected from the group consisting of alkyl, cycloalkyl, aryl and heteroaryl;

$R_{20}$ is alkyl, aryl, aralkyl or heteroaryl; and n and r are independently 1, 2, 3, or 4;

or a pharmaceutically acceptable salt thereof.

In certain embodiments, compounds useful in the methods herein are represented by the structure (Formula II):

(II)

wherein

(a) Y is selected from the group consisting of oxygen, sulfur and nitrogen substituted with a hydrogen;

(b) $R_1$, $R_2$, $R_3$, and $R_4$ are each independently selected from the group consisting of hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, and CONRR';

(c) $R_5$ is selected from the group consisting of hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, CONRR', a six-membered heteroaryl ring system containing 1 or 2 N, O, or S atoms; and a six-membered aryl ring system; and (d) $R_6$, and $R_7$ are each independently selected from the group consisting of hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, and CONRR', where R can be a wide variety of substituent groups such as alkyl or aryl, or $R_6$ and $R_7$ may be taken together to form a ring.

In certain embodiments, compounds useful in the methods herein are represented by the structure (Formula III):

(III)

wherein (a) Y is selected from the group consisting of sulfur and nitrogen substituted with a hydrogen;

(b) $R_1$ is selected from the group consisting of hydrogen and methyl;

(c) $R_2$ is selected from the group consisting of (i) hydrogen; (ii) chlorine; (iii) bromine; (iv) a ketone of the formula —C(O)CH$_3$, (v) a sulfonamide of the formula —SO$_2$NH$_2$, or —SO$_2$NCH$_3$CH$_3$;

(d) $R_3$, $R_4$, and $R_5$ are each independently selected from the group consisting of (i) hydrogen; (ii) methyl; (iii) a carboxylic acid of formula —(CH$_2$)$_2$—COOH; and (iv) $R_4$ and $R_5$ taken together may form a six-membered saturated carbon ring.

Such compounds, and the preparation thereof, are disclosed, e.g., in U.S. Pat. Nos. 6,573,293, 7,125,905, and 7,211,600, incorporated herein by reference.

Additional RTK inhibitors (e.g., c-kit inhibitors) include the compound

(also known as "SU5416", see, e.g., U.S. Pat. Nos. 6,573,293, 7,125,905, and 7,211,600).

In certain embodiments, the compound is a phosphatase (PP2A or PP1) inhibitor. Examples of selective or non-selective PP2A or PP1 inhibitors calyculin (including calyculin A), okadaic acid, and the like.

In certain embodiments, the compound is an inhibitor of p38 MAP kinase. Examples of selective or non-selective inhibitors of p38 MAP kinase include and In certain embodiments, the compound is an inhibitor of TGF-beta receptor. Examples of selective or non-selective inhibitors of TGF-beta receptor include:

In certain embodiments, the compound is an inhibitor of RNA-dependent protein kinase (PKR). Examples of selective or non-selective inhibitors of PKR include (8Z)-8-(3H-imidazol-4-ylmethylidene)-6H-pyrrolo[5,4-g][1,3]benzothiazol-7-one.

In another embodiment, the compound is an inhibitor of a protein kinase such as src or c-kit, e.g., is a src inhibitor or c-kit inhibitor such as (3Z)—N,N-dimethyl-2-oxo-3-(4,5,6,7-tetrahydro-1H-indol-2-ylmethylidene)-1H-indole-5-sulfonamide:

(also known as "SU6656") (see, e.g., U.S. Pat. Nos. 6,573,293, 7,125,905, and 7,211,600, incorporated herein by reference).

In another embodiment, the compound is an inhibitor of an RTK such as met receptor tyrosine kinase, e.g., is a selective met inhibitor such as (also known as "SU11274", see, e.g., U.S. Pat. Nos. 6,573,293, 7,125,905, and 7,211,600).

In addition, it has been found that increasing the activity of an enzyme selected from the group consisting of a cyclin dependent kinase (CDK), c-Jun N-terminal kinases 2 (JNK2), kinase insert domain receptor (KDR), spleen tyrosine kinase (SYK), and glycogen synthase kinase 3 (GSK3), can treat or prevent a neurodegenerative disease or disorder. In certain embodiments, the activity of an enzyme is increased by direct agonism of the enzyme, by increasing levels of an endogenous ligand for the enzyme, or by reducing the level or activity of an antagonist of the enzyme. In another embodiment, the activity of an enzyme is increased by increasing the amount or concentration of the enzyme in a cell or tissue, e.g., by overexpression of the gene coding for the enzyme.

Sunitinib

Sunitinib or N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide, is a receptor tyrosine kinase (RTK) inhibitor approved by the FDA and marketed for treatment of cancers. The preparation of sunitinib is disclosed in U.S. Pat. No. 6,573,293, incorporated herein by reference in its entirety. The term "sunitinib" as used hereinafter is to be interpreted broadly and comprises the free base form and the pharmaceutically acceptable addition salts of sunitinib, or of any stereoisomers thereof. The acid addition forms may be obtained by reaction of the base form with an appropriate acid. Appropriate acids comprise, for example, inorganic acids such as hydrohalic acids, e.g. hydrochloric or hydrobromic acid; sulfuric acid; nitric acid; phosphoric acid and the like; or organic acids such as, for example, acetic, propanoic, hydroxyacetic, 2-hydroxypropanoic, 2-oxopropanoic, ethanedioic, propanedioic, butanedioic, (Z)-butenedioic, (E)-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

Sunitinib has now been found to have neuroprotective and neurite-stimulating activity (as measured in an in vitro assay), with an ability to protect retinal ganglion cells (RGCs). Without wishing to be bound by any theory, it is believed that the neuroprotective activity of sunitinib may be useful in the treatment or prevention of glaucoma, optic nerve diseases, and other neurodegenerative disorders.

Screening Assays

The invention also relates to screening assays for identifying agents that have neuroprotectant activity. The screening method is also useful for identifying variants, binding or blocking agents, etc., which act as neuroprotectants.

Pharmaceutical Compositions

Pharmaceutical compositions and formulations of the present invention include pharmaceutical compositions of the neuroprotective compounds disclosed herein (e.g., sunitinib and salts thereof), that can be administered to a mammal, and can also include veterinary compositions, e.g., pharmaceutical preparations of the subject compounds suitable for veterinary uses, e.g., for the treatment of livestock or domestic animals, e.g., dogs.

In one embodiment, the methods and compositions of the present invention comprise sunitinib and/or pharmaceutically acceptable salts thereof, such as the malate salt.

The invention provides for compositions comprising a compound according to the invention, for example sunitinib, admixed with a physiologically compatible carrier. As used herein, "physiologically compatible carrier" refers to a physiologically acceptable diluents such as water, phosphate buffered saline, or saline, and further may include an adjuvant. Adjuvants such as incomplete Freund's adjuvant, aluminum phosphate, aluminum hydroxide, or alum are materials well known in the art.

Methods of introduction may be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a subject compound at a particular target site.

The preparations of the present invention may be given orally, parenterally, topically, or rectally. They are of course given by forms suitable for each administration route. For example, they are administered in tablets or capsule form, by injection (including intravitreal injection), inhalation, eye lotion, ointment, suppository, controlled release patch, etc. administration by injection, infusion or inhalation; topical by lotion or ointment; and rectal by suppositories.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the subject.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Additional ingredients may be added to the topical composition, as long as they are pharmaceutically acceptable and not deleterious to the epithelial cells or their function. Further, they should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like may be present. The pH of the topical composition of this invention may be adjusted to a physiologically acceptable range of from about 6.0 to about 9.0 by adding buffering agents thereto in order for the composition to be physiologically compatible with the skin Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder, optionally including additives such as 1 mM-50 mM histidine, 0.1%-2% sucrose, 2%-7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition with information including amount, frequency and method of administration.

The invention also includes the use of a compound such as an flt3 inhibitor, a phosphatase (PP2A or PP1) inhibitor, a p38 MAP kinase inhibitor, a TGF-beta receptor inhibitor, c-kit inhibitor, src inhibitor, RNA-dependent protein kinase inhibitor, or sunitinib (or a salt thereof) in the manufacture of a medicament for neuroprotection.

Combination Therapy

In certain embodiments, the invention contemplates combination therapies. For example, an flt3 inhibitor such as sunitinib can be used in therapy in combination with other compounds. For example, sunitinib can be co-administered in combination with other compounds, for example, at a ratio in the range of 1:1-1:5-5:1, 1:1-1:10-10:1, 1:1-1:25-25:1, 1:1-1:100-100:1, 1:1-1:1000-1000:1 or 1:1-1:10,000-10,000:1. For example, in the treatment of glaucoma, other anti-glaucoma medicaments can be used, such as: beta-blockers, including levobunolol (Betagan), timolol (Betimol, Timoptic), betaxolol (Betoptic) and metipranolol (OptiPranolol); alpha-agonists such as apraclonidine (Iopidine) and brimonidine (Alphagan); carbonic anhydrase inhibitors, such as acetazolamide, methazolamide, dorzolamide (Trusopt) and brinzolamide (Azopt); prostaglandins or prostaglandin analogs such as latanoprost (Xalatan), bimatoprost (Lumigan) and travoprost (Travatan); miotic or cholinergic agents, such as pilocarpine (Isopto Carpine, Pilopine) and carbachol (Isopto Carbachol); epinephrine compounds, such as dipivefrin (Propine); forskolin; or neuroprotective compounds such as brimonidine and memantine. In certain embodiments, the compound used in combination with an flt3 inhibitor such as sunitinib is not an anti-angiogenic agent such as a steroid derivative such as 2-methoxyestradiol or analogs or derivatives thereof.

Other combination therapies contemplated by the invention includes treatment with sunitinib in combination with surgery, e.g., surgical relief of intraocular pressure, e.g., via trabeculectomy, laser trabeculoplasty, or drainage implants.

Dosage and Mode of Administration

As described, these compounds may be administered to humans and other animals for therapy by any suitable route of administration, including orally, nasally, or ocularly, as by, for example, a spray, rectally, intravaginally, parenterally, intracisternally and topically, as by powders, ointments or drops (including eyedrops), including buccally and sublingually. For example, for ocular administration, an eyedrop formulation can include an effective concentration of a compound of the invention together with other components such as buffers, wetting agents and the like. Intravitreal injection may also be employed to administer a compound to the eye.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, doses of the compounds of this invention for a patient will range from about 0.0001 to about 1000 mg per kilogram of body weight per day. In certain embodiments, the dosage is between about 1 µg/kg and about 500 mg/kg, more preferably between about 0.01 mg/kg and about 50 mg/kg. For example, in certain embodiments, a dose can be 1, 5, 10, 15, 20, or 40 mg/kg/day.

If desired, the effective daily dose of the active compound may be administered as two, three, four, five, six or more sub-doses administered separately at appropriate intervals throughout the day, optionally, in unit dosage forms.

The patient receiving this treatment is any animal in need, including primates, in particular humans, and other mammals such as equines, cattle, swine and sheep; and poultry and pets in general. An animal in need, in preferred embodiments, is a subject suffering from or susceptible to a neurodegenerative disease or disorder such as glaucoma, e.g., a subject diagnosed as suffering from or susceptible to a neurodegenerative disease or disorder.

The compound of the invention can be administered as such or in admixtures with pharmaceutically acceptable and/or sterile carriers and can also be administered in conjunction with other agents such as antibiotics, neuroprotectants, and other therapeutic agents. Conjunctive therapy thus includes sequential, simultaneous and separate administration of the active compound in a way that the therapeutic effects of the first administered one is not entirely disappeared when the subsequent is administered.

The dosage range for administration will be adjusted by the physician as necessary.

Therapeutic Methods

Preferred compounds and amounts for use in the therapeutic methods of the invention produce at least about 10% to 15% decrease in cell loss or loss of function relative to cell survival or cell function measured in absence of the tested compound in an assay, more preferably at least about a 20% or 25% decrease relative to a control, and still more preferably induce at least about 20%, 30%, 40%, 50%, 60%, 70%, 80%, 90% or 100% decrease in cell loss or loss of function relative to absence of the tested compound in such an assay. In other embodiments, the preferred compounds and amounts for use in the therapeutic methods of the invention produce at least about 10% to 15% increase in neuron count, neuron function, neurite count, neurite total length, or neurite average length relative to absence of the tested compound in an assay.

The methods of the invention can be used to treat any neurodegenerative disease or disorder (including traumatic injury) in which neuronal cell loss is implicated, or in which damage to neurites is involved. Thus, for example, the methods of the invention can be used to treat neurodegenerative disorders such as or associated with alcoholism, Alexander's disease, Alper's disease, Alzheimer's disease, amyotrophic lateral sclerosis (Lou Gehrig's Disease), ataxia telangiectasia, Batten disease (also known as Spielmeyer-Vogt-Sjogren-Batten disease), bovine spongiform encephalopathy (BSE), Canavan disease, Cockayne syndrome, corticobasal degeneration, Creutzfeldt-Jakob disease, frontotemporal lobar degeneration, Huntington's disease, HIV-associated dementia, Kennedy's disease, Krabbe's disease, Lewy body dementia, neuroborreliosis, Machado-Joseph disease (Spinocerebellar ataxia type 3), Multiple System Atrophy, multiple sclerosis, Niemann Pick disease, Parkinson's disease, Pelizaeus-Merzbacher Disease, Pick's disease, primary lateral sclerosis, prion diseases, Progressive Supranuclear Palsy, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), spinal muscular atrophy, Steele-Richardson-Olszewski disease, and tabes dorsalis. In addition, methods of the invention can be used to treat neuronal damage due to traumatic injury or stroke (e.g., by preventing death of damaged neuronal cells and/or by promoting or stimulating neurite growth from damaged neuronal cells).

In certain embodiments, the method can be used to treat glaucoma, including primary open angle glaucoma (POAG), and angle closure glaucoma, as well as normal tension glaucoma and secondary glaucomas. In certain embodiments, the glaucoma is not neovascular glaucoma.

In certain embodiments, the subject has been identified (e.g., diagnosed) as suffering from or susceptible to a neurodegenerative disease or disorder (including traumatic injury) in which neuronal cell loss is implicated, or in which damage to neurites is involved, and for which treatment or prophylaxis is desired. In certain embodiments, the subject is not suffering, or has not been diagnosed as suffering, from cancer. In certain embodiments, the subject is not suffering, or has not been diagnosed as suffering, from a disorder related to excess angiogenesis. In certain embodiments in which a cell is contacted with sunitinib, or a pharmaceutically acceptable salt, the cell is not a neoplastic cell. In certain embodiments of the above aspects, the cell is a mammalian cell, more preferably a human cell.

In certain embodiments, the present methods are applicable to cell culture techniques wherein it is desirable to prevent neuronal cell death or loss of neuronal function. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of certain embodiments of the present methods is in cultures of neuronal cells, such as in the use of such cultures for the generation of new neurons and glia. In such embodiments of the subject methods, the cultured cells can be contacted with a compound of the present invention in order to prevent neuronal cell death or loss of neuronal function. In an exemplary embodiment, the subject method can be used to culture, for example, sensory neurons or, alternatively, motoneurons. Such neuronal cultures can be used as convenient assay systems as well as sources of implantable cells for therapeutic treatments.

In certain embodiments, the methods of the invention can be used to improve the survival or integration of transplanted neuronal cells into a host subject. Thus, for example, a subject receiving a transplant of neuronal cells can be treated (before, during, or after the transplantation procedure) with compounds according to the methods of the present invention, to prevent cell death of the transplanted cells (or host cells that may be perturbed during the transplantation procedure), and/or to promote the growth of neurites in the transplanted cells or the host neuronal cells, and thereby promote integration of the transplanted cells into the host nervous system.

Kits or Pharmaceutical Systems

The present compounds and compositions may be assembled into kits or pharmaceutical systems for use in treatment of neurodegenerative diseases, disorders, or conditions. Kits or pharmaceutical systems according to this aspect of the invention include a compound as described herein (e.g., sunitinib or a pharmaceutically acceptable salt thereof), preferably in unit dosage form. The compound may be present together with a pharmaceutically acceptable solvent, carrier, excipient, or the like, as described herein.

The kits or pharmaceutical systems of the invention may also include associated instructions for using the compounds of the invention for treating a neurodegenerative disease or disorder. The instructions will generally include information about the use of the compound for treatment of a disease or disorder or symptoms thereof; in preferred embodiments, the instructions include at least one of the following: description of the active compound; dosage schedule and administration for treatment of a neurodegenerative disease or disorder; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The kit may also include one or more container means, such as vials, tubes, ampules, bottles and the like, for containing the compound (and optionally carried within a carrier means, such as a box, carton, tube or the like). Such containers can be made of plastic, glass, laminated paper, metal foil, or other materials suitable for holding medicaments.

EXAMPLES

Example 1: Sunitinib Treatment Increases RGC Count and Neurite Length In Vitro

In this Example, sunitinib and other compounds were administered to retinal ganglion cells (RGCs) in cell culture to determine the effects of the compounds on neuronal count and neurite growth.

We established a robust high-content screening system combining the immunopanning- or other immunobead-based purification of primary mouse and rat RGCs and automated fluorescence-based imaging analysis (see, e.g., U.S. Patent Publication No. 2007/0185069, incorporated herein by reference). To enhance the assay sensitivity, the culture condition is defined to support a baseline level of RGC viability (20~60% surviving RGCs after three days in culture) and neurite growth by 2.5 µM forskolin. By adapting this system, we have taken diversity-oriented approach and screened ~6,000 small molecules from a compound library.

Figure 1A:
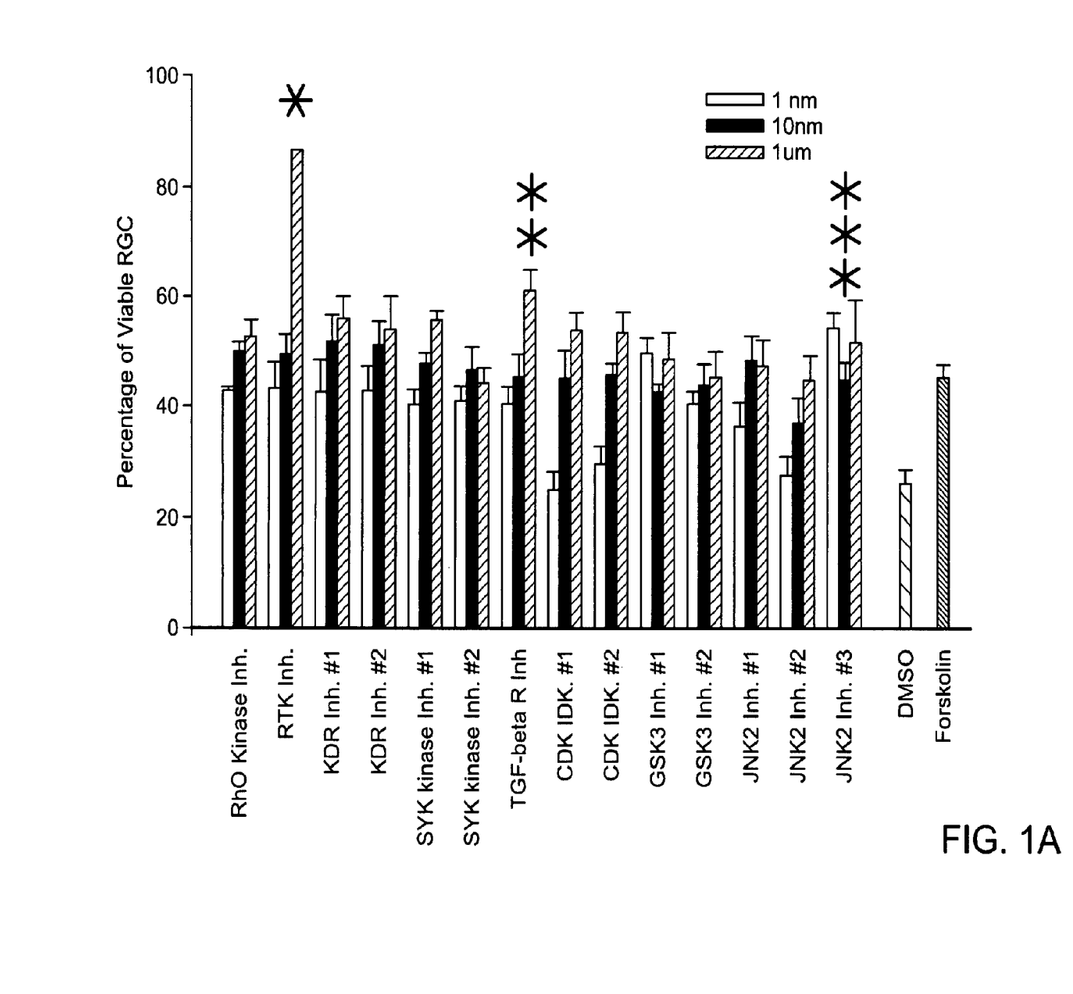
Figure 1B:
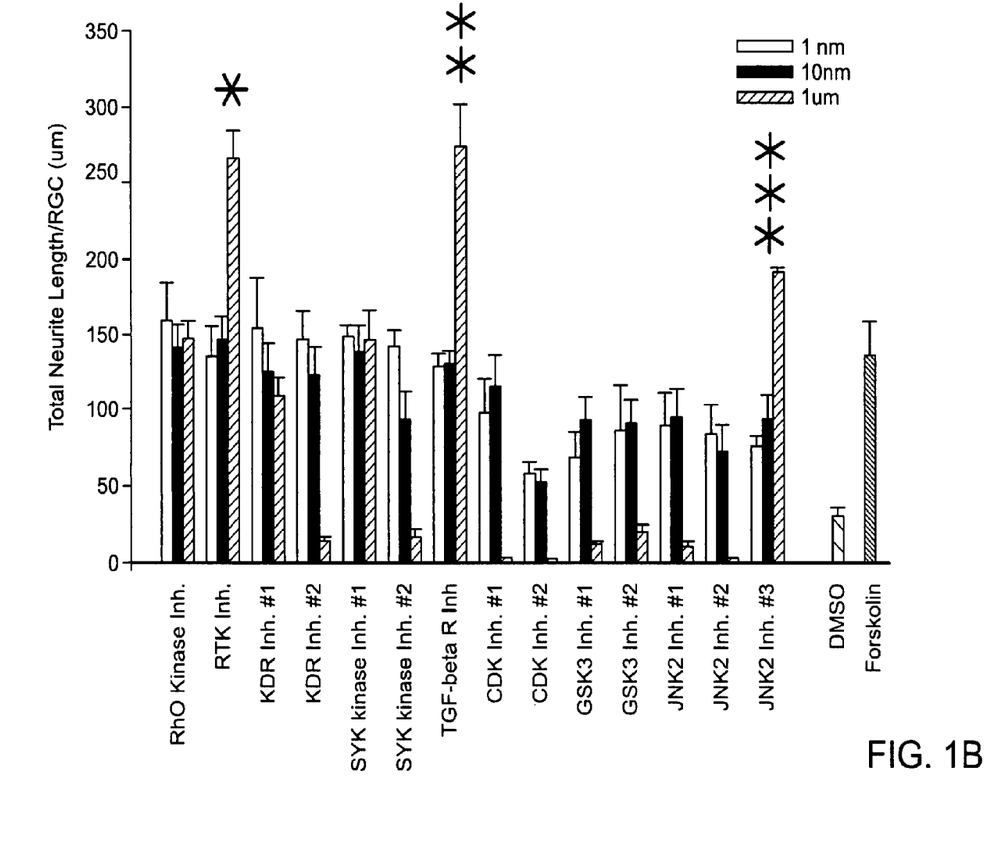
Figure 2A:
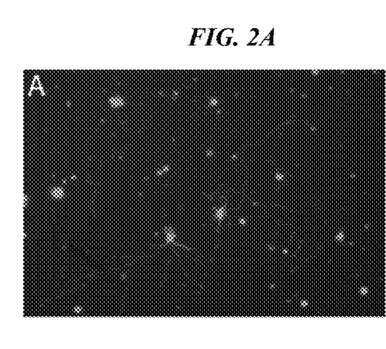
FIG. 2A-FIG. 2F show that sunitinib promotes RGC survival and neurite growth in vitro.
Figure 2B:
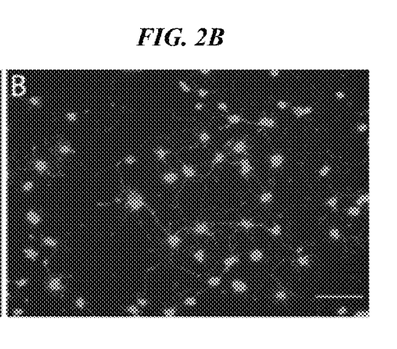
Figure 2C:
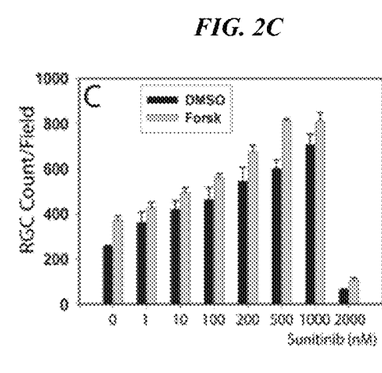
Figure 2D:
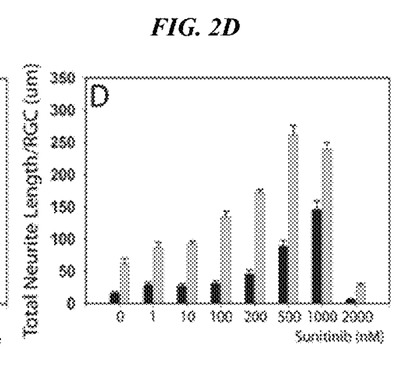
Figure 2E:
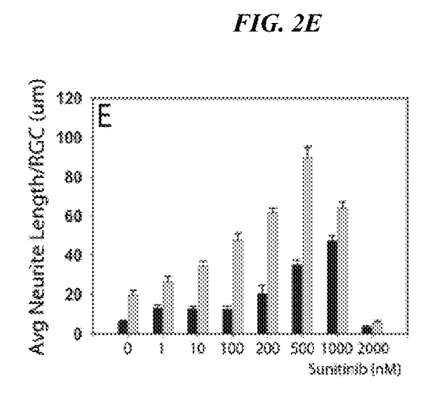
Figure 2F:
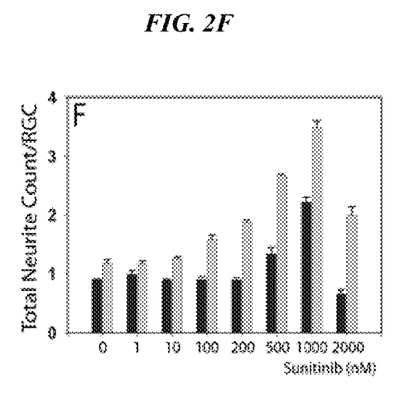

In parallel, we also performed target-oriented screening in hope of identifying more relevant bioactivities. Since kinases are important signaling molecules modulating in a large diversity of cellular events including neuronal survival and neurite growth, we prioritized a mini-screening of a collection of kinase inhibitors. Unexpectedly but most significantly, one of the receptor tyrosine kinase (RTK) inhibitors, sunitinib, showed a very strong activity in promoting RGC survival. Additionally, it markedly stimulated RGC neurite growth by nearly two fold of the baseline level. Among other kinase inhibitors, JNK2 inhibitor #3 showed similar neurite-promoting activity but had little effect on RGC survival (see, e.g., FIG. 1). Transforming Growth Factor β (TGFβ) receptor inhibitor strongly stimulated neurite growth while only modestly helped RGC survival. Several kinase inhibitors, such as CDK inhibitor #1 and 2, and JNK2 Inhibitor #1 and 2, appeared to negatively regulate both RGC survival and neurite growth, whereas others (e.g. KDR inhibitor #1 & #2, SYK inhibitor #2, and GSK3 inhibitor #1 and #2) inhibited neurite outgrowth but did not have a significant effect on RGC survival. Kinase inhibitors are well known for having issues with specificity (or lack thereof), and this needs to be taken into consideration in interpreting these results. Nonetheless, taken together, these results not only identify a number of interesting activities but also demonstrate the ability of the assay to quantify several distinct RGC cellular behaviors.

As mentioned above, in contrast to its anti-cancer activity, sunitinib shows very strong neuroprotective and neurite-promoting effects on mouse RGCs in vitro, and both effects appear to be dosage-dependent, with the peak activities at 1 µM and 500 nM, respectively. Presence of forskolin in the media can moderately help sunitinib improving RGC survival and strongly enhancing neurite growth. Sunitinib appeared to promote neurite growth by increasing neurite numbers as well as their average length, suggesting its positive regulation on RGC neurite specification as well as elongation (see, e.g., FIG. 2).

The neuroprotective activity of sunitinib on primary mouse RGC is the strongest among the large number of chemical agents that we screened. We compared its effect with several common biological factors including BDNF, CNTF, BDNF+CNTF, PGDF AA, PDGF BB, and Oncomodulin plus mannose. Sunitinib shows a much stronger protective effect on RGCs than any of these trophic factors. Its neurite-promoting activity is also significantly stronger than the otherwise most potent Oncomodulin plus mannose regimen.

Figure 3:
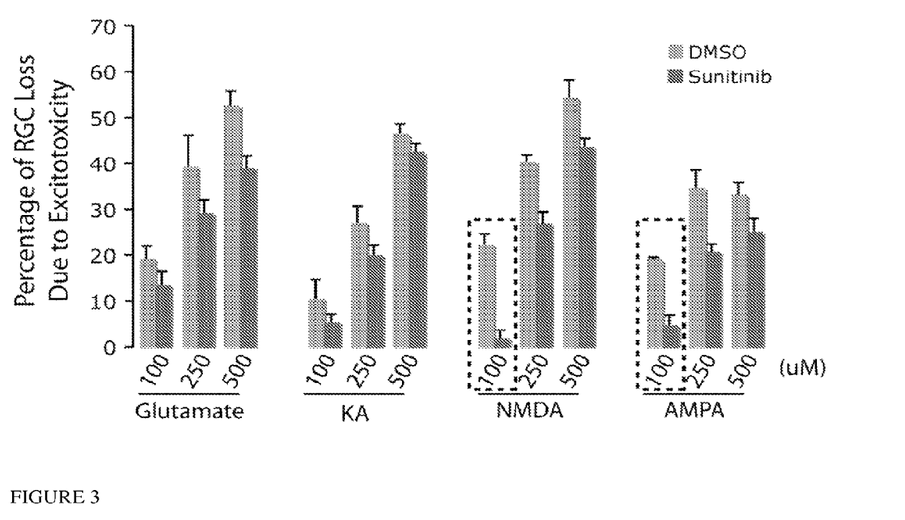
FIG. 3 shows that sunitinib treatment protects against NMDA excitotoxicity in vitro.

Example 2: Sunitinib Treatment Protects Against NMDA Excitotoxicity In Vitro We sought to determine whether sunitinib may provide beneficial support to RGC survival under the experimentally created pathological condition. Neuronal toxicity of excitatory amino acid glutamate and its analogue NMDA is implicated in a number of neurodegenerative conditions that involve RGC, such as glaucoma, optic neuropathies of trauma and other origins, and that affect other CNS structures, such as Alzheimer's disease, Parkinson's disease, Huntington's disease, stroke, and amyloid lateral sclerosis (ALS). Although the vulnerability of rodent RGC to excitotoxicity has been demonstrated in many in vitro and in vivo studies, there are a few reports suggesting that rodent RGCs may be resistant to glutamate excitotoxicity. Nevertheless, we used our culture conditions to verify whether mouse RGCs are sensitive to excitotoxicity, and to examine whether sunitinib can render primary mouse RGC resistance to glutamate excitotoxicity. The purified mouse RGCs were seeded with or without of 1 µM sunitinib for 16 hours prior to a 5-hour exposure to three different concentrations (100 µM, 250 µM, 500 µM) of glutamate, kainite acid (KA), NMDA, and AMPA. RGC viability was measured and the percentage of RGC loss due to the excitotoxicity was calculated. Regardless of the presence of sunitinib in the media, all the four excitatory glutamate receptor agonists showed strong and dosage-dependent damage to mouse RGC at these relatively high concentrations. Sunitinib invariably antagonized the detrimental effect of glutamate and its analogues. In particular, sunitinib markedly reduced the RGC loss caused by 100 µM of NMDA and AMPA by ~10 and 4 folds, respectively (see, e.g., FIG. 3). The strong protective activity elicited by sunitinib against RGC excitotoxicity further underscores its potential therapeutic value in the management of the excitotoxicity-associated neurodegenerative conditions.

Example 3: Sunitinib Treatment Protects Against Axon-Injury Induced RGC Cell Death In Vivo Given our finding that sunitinib exhibits strong neuroprotective effect on RGC in the setting of NMDA excitotoxicity in vitro, we next examined whether sunitinib could elicit similar protective activity in vivo. Mouse optic nerve crush is a well-established animal model in mimicking the pathological conditions in which the primary injury sites are focal to RGC axons such as in glaucoma, AION, traumatic optic neuropathy, and multiple sclerosis. Specific RGC loss following nerve crush, which largely spares displaced amacrine cells in GCL, is thought to result from incomplete understood mechanism that implicates the blockage of retrograde axonal transport and subsequently impaired neurotrophin signaling, and excitotoxicity etc. In addition, mouse optic nerve crush has been successfully employed as an experimental system to identify the genetic nature controlling RGC susceptibility to axon injury.

During the procedure, the optic nerve was carefully exposed through a post-orbital approach, and crushed with a self-closing forceps for three seconds. This resulted in an ~25.2% of cell loss in GCL within ten days (~74.8% remaining, data not shown). Since RGCs populate ~60% cells in rodent GCL, the estimated surviving RGC is ~57.3%. We adapt the mouse optic nerve crush to assess the neuroprotective activity of sunitinib in vivo. Among five different dosages (5, 10, 15, 20, 40 mg/kg/day), we observed that ~88.5% cells in GCL survived with the systemic administration of 5 mg/kg/day for ten days (data not shown), and hence a projected 79.2% surviving RGCs (P<0.007). The observation strongly suggests that low-dose sunitinib (5 mg/kg/day) can effectively protect mouse RGCs from axon injury induced cell death. The treatment with higher dosages exhibited less or no neuroprotective effect to RGCs, perhaps because, although 1 µM sunitinib is beneficial to RGC survival in vitro, higher concentrations exhibit toxicity, and the lipophilic property and long half-life of sunitinib may lead to its excessive accumulation in the retina. In fact, we found that ten-day treatment of sunitinib at 15 mg/kg/day or higher dose yields an obvious yellow appearance (same color as sunitinib) in both normal and diseased retinas. Nevertheless, our in vivo trial with a preclinical RGC axon injury model suggests that systemic administration of a carefully chosen low dosage of sunitinib can significantly reduce RGC loss secondary to optic nerve injury.

Apoptosis has been identified as the major form of RGC death in many, if not all, degenerative conditions targeting their axons, and in mouse optic nerve. Three days following the nerve crush, a large number of activated Caspase-3 positive cells emerged in the GCL. By systemic sunitinib treatment, the number of apoptotic cells in GCL is significantly reduced by 38.9% (data not shown). These findings support that the neuroprotective activity of sunitinib may depend on its ability in blocking or attenuating the activation of apoptotic pathway(s).

Additional in vivo studies in the optic nerve crush model showed that intravitreal injection of sunitinib is also capable of reducing RGC loss secondary to optic nerve injury.

Taken together, our in vitro and in vivo studies strongly suggested that sunitinib, an anti-cancer drug that was designed for the purpose of targeting multiple RTKs, can be used as a promising neuroprotectant in managing RGC death secondary to the pathological assaults to their axons.

Example 4: Effect of Treatment with Other Protein Kinase Inhibitors

Using purified primary mouse RGC culture, we examined nine protein kinase inhibitors that are currently in clinical practice or trials. None except Lestaurtinib showed significant pro-surviving activity on RGCs, albeit to a lesser extent than sunitinib. Interestingly, in contrast to sunitinib, Lestaurtinib appeared to be inhibitory to RGC neurite growth. Although it is unclear how many common and unique protein kinases and off-targets are targeted by Lestaurtinib and sunitinib, FLT3 is indeed one primary target of both inhibitors (IC50 for sunitinib, 50 nM; for Lestaurtinib, 5 nM).

Among other inhibitors, Dasatinib can suppress both RGC survival and neurite growth, and Sorafenib at 100 nM can stimulate neurite growth as potently as sunitinib (1 µM). However, Sorafenib is different from sunitinib in lacking strong protective activity to RGC. FLT3 is also a shared target between Sorafenib (IC50=58 nM) and sunitinib. Nevertheless, in contrast to sunitinib, Sorafenib may also target several cytosolic protein kinases such as CRAF and BRAF, which may explain the difference in pro-survival effects between the two inhibitors.

As an inhibitor targeting multiple RTKs, sunitinib exhibits unexpected but strong protective and neurite-promoting activities on RGCs. This may imply that baseline level of certain kinase pathway(s) may "actively" kill RGCs in culture or in the setting of optic nerve injury.

Example 5

To examine whether sunitinib could attenuate or reverse the potential detrimental signals from RTK ligand(s), we started with Flt3 ligand (Flt3l). We found that Flt3l at 16 ng/ml, a concentration four times its EC50, can reduce RGC survival by 38.3%, but does not do so at its EC50 of 4 ng/ml, suggesting that a nearly full activation of Flt3 is required for sunitinib's RGC toxicity. When sunitinib was present in the media, it partially but significantly antagonized the detrimental effects of Flt3l at 16 ng/ml on RGC by 1.4 fold. Interestingly, although Flt3l at 4 ng/ml did not appear to affect RGC survival, it did compromise the pro-surviving activity of sunitinib by 36.6%, suggesting that a low level of Flt3l, though insufficient to kill RGC, can antagonize sunitinib's protective effect. Without wishing to be bound by theory, this finding suggests that Flt3 pathway activation can negatively affect RGC survival in vitro. This finding also implies that the neuroprotective activity of sunitinib can be at least partially attributed to its ability in blocking Flt3 pathway.

Example 6

Figure 4:
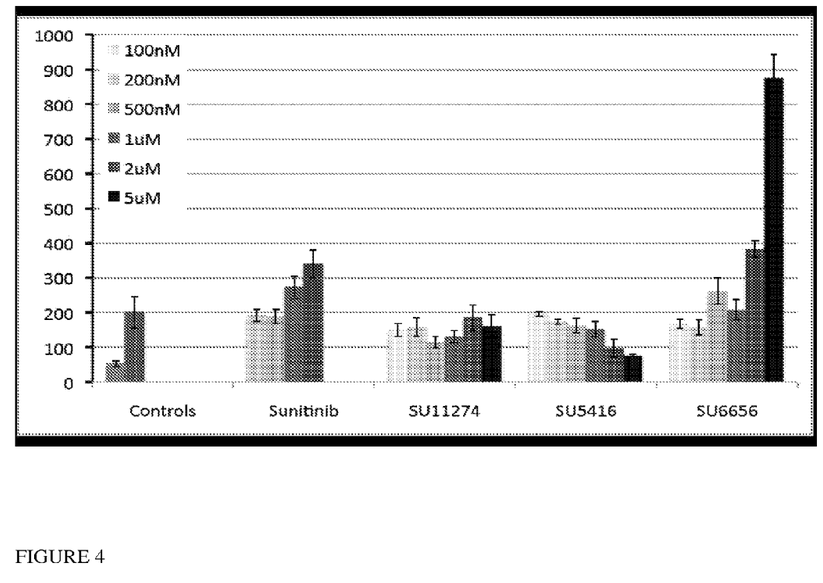
FIG. 4 shows the effect of sunitinib, SU11274, SU5416 or SU6656 on RGC survival.

Mouse retinal ganglion cells (RGCs) were purified and then grown in culture for approximately 2 days in the presence or absence of various concentrations of compounds (sunitinib, SU6656, SU11274, SU 5416). At the end of the culture period, live-dead and neurite outgrowth assays were performed and the stained cells were analyzed with a Cellomics VTI HCS reader and Cellomics image analysis software. As seen in FIG. 4, in which live cell count numbers are shown on the Y-axis, both Sunitinib and SU6656 significantly increased RGC survival.

Example 7

An in vivo study using the optic nerve crush model (see Example 3, supra) showed that intravitreal injection of a TGF-beta receptor inhibitor is also capable of reducing RGC loss (stimulate RGC regeneration) after optic nerve injury. The compound of the following structure was used:

Intravitreal injection of 1 µl of this commercially-available compound (2 mM) every three days for nine days showed increased RGC survival.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of treating a neurodegenerative disease or disorder, the method comprising administering to a subject in need thereof an effective amount of a pharmaceutical composition consisting essentially of a compound selected from the group consisting of sunitinib, SU11274, SU5416, or SU6656, or a pharmaceutically acceptable salt thereof, thereby treating the neurodegenerative disease or disorder.

2. The method of claim 1, wherein the neurodegenerative disease or disorder is glaucoma.

3. The method of claim 1, wherein the glaucoma is not neovascular glaucoma.

4. The method of claim 1, wherein the subject is a mammal.

5. The method of claim 1, wherein the subject is a human.

6. The method of claim 1, further comprising the step of monitoring the subject to determine the efficacy of treatment.

7. The method of claim 1, wherein the neurodegenerative disease or disorder is wet macular degeneration.

8. The method of claim 1, wherein the neurodegenerative disease or disorder is dry macular degeneration.

* * * * *

UNITED STATES PATENT AND TRADEMARK OFFICE
CERTIFICATE OF CORRECTION

PATENT NO. : 9,655,882 B2
APPLICATION NO. : 14/626524
DATED : May 23, 2017
INVENTOR(S) : Donald J. Zack et al.

It is certified that error appears in the above-identified patent and that said Letters Patent is hereby corrected as shown below:

In the Specification

Column 1, Line 20-22 second paragraph (government support statement) please replace with the following:
STATEMENT OF GOVERNMENTAL INTEREST
This invention was made with government support under grant number EY017155, awarded by the National Institutes of Health. The government has certain rights in the invention.

Signed and Sealed this
Sixth Day of February, 2018

Joseph Matal
*Performing the Functions and Duties of the
Under Secretary of Commerce for Intellectual Property and
Director of the United States Patent and Trademark Office*